US007005284B1

(12) United States Patent
Ikeda et al.

(10) Patent No.: US 7,005,284 B1
(45) Date of Patent: Feb. 28, 2006

(54) TRANSALDOLASE GENE

(75) Inventors: Masato Ikeda, Machida (JP); Yutaka Takano, Machida (JP); Tetsuo Nakano, Ube (JP); Nozomu Kamada, Machida (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 144 days.

(21) Appl. No.: 10/088,594

(22) PCT Filed: Sep. 21, 2000

(86) PCT No.: PCT/JP00/06471

§ 371 (c)(1),
(2), (4) Date: Mar. 21, 2002

(87) PCT Pub. No.: WO01/21774

PCT Pub. Date: Mar. 29, 2001

(30) Foreign Application Priority Data

Sep. 21, 1999  (JP)  ............................ 11/266548

(51) Int. Cl.
C12N 9/10 (2006.01)
C12N 1/20 (2006.01)
C12N 15/00 (2006.01)
C07K 1/00 (2006.01)
C07H 21/04 (2006.01)

(52) U.S. Cl. .................. 435/193; 435/183; 435/252.3; 435/320.1; 530/350; 536/23.2

(58) Field of Classification Search ............... 435/69.1, 435/183, 193, 252.3, 252.32, 320.1; 530/350; 536/23.2

See application file for complete search history.

(56) References Cited

U.S. PATENT DOCUMENTS 5,643,758 A * 7/1997 Guan et al. ................. 435/69.7
6,797,509 B1 * 9/2004 Dunican et al. .......... 435/252.3

FOREIGN PATENT DOCUMENTS

| WO | 98/18936 | 5/1998 |
| WO | WO 98/18936 | 5/1998 |
| WO | WO 01 00844 | 1/2001 |
| WO | WO 01/04325 | 1/2001 |

OTHER PUBLICATIONS

Miyamoto et al. Accession AAR63573. Jun. 5, 1995.*

Attwood et al. Which craft is best in bioinformatics? Comput. Chem. 2001, vol. 25(4), pp. 329-339.*
Ponting, C.P. Issues in predicting protein function from sequence. Brief. Bioinform. Mar. 2001, vol. 2(1), pp. 19-29.*
Alignment No. 1. Dunican et al. US Patent 6,797,509.*
Alignment No. 2. Dunican et al. US Patent 6,797,509.*
Ikeda, et al., "Hyperproduction of Tryptophan by Corynebacterium Glutamicum with th Modified . . . ", Applied and Environmental Microbiology, vol. 65, No. 6 (1999), pp. 2497-2502.
Ikeda, et al., "Cloning of the Transketolase Gene and the Effect of its Dosage on Aromatic . . . ", Applied Microbiol. and Biotech., vol. 51 (1999), pp. 201-206.
GeneBank Accession No. D13159.
Sprenger, "Genetics of pentose-phosphate pathway enzymes . . . ", Arch Microbiol., vol. 164 (1995), pp. 324-330.
Cole, et al., Deciphering the biology of Mycobacterium tuberculosis from the complet genome sequence, Nature (1998), vol. 293, pp. 537-544.
Kohler, et al., "Transaldolase genes from the cyanobacteria . . . ", Plant Molecular Biology, vol. 30 (1996), pp. 213-218.
Moradian, et al., "A Biomimetric Biotechnological Process for Converting Starch . . . ", J. Am. Chem. Soc., vol. 114 (1992), pp. 6980-6987.

* cited by examiner

Primary Examiner—Manjunath N. Rao
Assistant Examiner—Christian L. Fronda
(74) Attorney, Agent, or Firm—Fitzpatrick, Cella, Harper & Scinto

(57) ABSTRACT

Attempts are made to provide a novel transaldolase gene; a polypeptide encoded by this gene; a recombinant DNA obtained by integrating this gene; a microorganism carrying this recombinant DNA; and a process for producing an aromatic amino acid, an aromatic vitamin, L-histidine, riboflavin, a nucleic acid, a nucleic acid-associated substance, a novel saccharide, etc. by using the above microorganism. As the results of extensive studies, a novel transaldolase gene is isolated from chromosomal DNA of a microorganism belonging to the genus Corynebacterium as a DNA fragment complementary to the requirement for shikimic acid of a transketolase defective variant obtained as a variant with the requirement for shikimic acid belonging to the genus Corynebacterium. Further, a recombinant DNA containing this gene is constructed and transferred into a host microorganism, thereby achieving the objects as described above.

5 Claims, No Drawings

TRANSALDOLASE GENE

TECHNICAL FIELD

The present invention relates to a novel transaldolase gene, and to a polypeptide encoded by the gene, a recombinant DNA obtained by ligating the gene, a transformant carrying the recombinant DNA, and a process for producing the polypeptide, aromatic amino acids, aromatic vitamins, L-histidine, riboflavin, nucleic acids, nucleic acid-associated substances, novel saccharides and others by utilizing the transformant.

BACKGROUND ART

Transaldolase is an enzyme involved in pentose phosphate pathways, and plays an important role in biosynthesis and metabolism of aromatic compounds such as aromatic amino acids and aromatic vitamins, nucleic acid-associated substances such as purine-nucleotide and pyrimidine-nucleotide, as well as L-histidine, riboflavin and others [*Arch. Microbiol.*, 164, 324 (1995)]. Accordingly, a transaldolase gene and its gene products are useful as the target in breeding microorganisms for efficient fermentation and production of the metabolites.

As for transaldolase-encoding DNAs, an *Escherichia coli*-derived gene [Gene Bank Accession Number D13159], a *Mycobacterium tuberculosis*-derived gene [*Nature*, 393, 537 (1998)], and *Cinecococcus*-derived gene [*Plant Mol. Biol.*, 30, 213 (1996)] were isolated; and their nucleotide sequences were determined.

It is reported that the productivity of aromatic compounds in *Escherichia coli* is increased when its transaldolase activity is increased (WO98/18936).

However, for microorganisms belonging to the genus *Corynebacterium* that are widely used in amino acid fermentation of industrial importance, there is no report relating to the transaldolase gene and the enzyme encoded by the gene, and the nucleotide sequence of that gene is not known at all.

Regarding saccharide synthesis using transaldolase, an example is reported in which the enzyme is used for producing D-fructose from processed starch [*J. Am. Chem. Soc.*, 114, 6980 (1992)].

DISCLOSURE OF THE INVENTION

The object of the present invention is to provide a novel transaldolase gene, as well as a polypeptide encoded by the gene, a recombinant DNA obtained by ligating the gene, a transformant carrying the recombinant DNA, and a process for producing the polypeptide, aromatic amino acids, aromatic vitamins, L-histidine, riboflavin, nucleic acids, nucleic acid-associated substances, novel saccharides and others by using the transformant.

To achieve the object as mentioned above, the present inventors have used various techniques of DNA recombination and extensively studied the chromosomal genes of microorganisms belonging to the genus *Corynebacterium*. As a result, the present inventors have found that a transaldolase gene exists adjacent to the 3'-downstream site of a gene encoding transketolase, an enzyme differing from transaldolase, in a pentose phosphate pathway, and the present inventors have found the fact first. On the basis of this finding, the present invention has been completed. Specifically, the invention relates to the following subject matters (1) to (16):

(1) A polypeptide comprising the amino acid sequence of SEQ ID NO: 1.
(2) A polypeptide comprising the amino acid sequence of SEQ ID NO: 1 in which one or more amino acids have been substituted, deleted or added, and having transaldolase activity.
3) A polypeptide comprising an amino acid sequence which is at least 60% homologous to the amino acid sequence of SEQ ID NO: 1, and having transaldolase activity.
(4) A DNA coding for the polypeptide of any one of above (1) to (3).
(5) A DNA comprising the nucleotide sequence of SEQ ID NO: 2.
(6) A DNA which hybridizes with the DNA of above (4) or (5) under stringent conditions, and codes for a polypeptide having transaldolase activity.
(7) A recombinant DNA obtainable by ligating the DNA of any one of above (4) to (6) with a vector.
(8) A transformant carrying the recombinant DNA of above (7).
(9) A transformant in which one or more nucleotides have been substituted, deleted or inserted in the nucleotide sequence of the DNA of any one of above (4) to (6) carried by the transformant of above (8) or in the nucleotide sequence of a DNA existing upstream the DNA and participating in transcription and translation, and of which the transaldolase activity is enhanced over that of the transformant not having undergone the substitution, deletion or insertion.
(10) The transformant of above (8) or (9), wherein the transformant has an ability to produce an aromatic amino acid or aromatic vitamin.
(11) A process for producing an aromatic amino acid or aromatic vitamin, which comprises culturing the transformant of above (10) in a medium to thereby produce and accumulate in the culture the aromatic amino acid or aromatic vitamin, and recovering the aromatic amino acid or aromatic vitamin from the culture.
(12) A transformant in which one or more nucleotides have been substituted, deleted or inserted in the nucleotide sequence of the DNA of any one of above (4) to (6) carried by the transformant of above (8) or in the nucleotide sequence of a DNA existing upstream the DNA and participating in transcription and translation, and of which the transaldolase activity is lowered below that of the transformant not having undergone the substitution, deletion or insertion, or of which the transaldolase activity is lost.
(13) The transformant of above (8) or (12), wherein the transformant has an ability to produce a substance selected from L-histidine, riboflavin, nucleic acids and nucleic acid-associated substances.
(14) A process for producing a substance selected from L-histidine, riboflavin, nucleic acids and nucleic acid-associated substances, which comprises culturing the transformant of above (13) in a medium to thereby produce and accumulate the substance in the culture, and recovering the substance from the culture.
(15) A process for producing the polypeptide of any one of above (1) to (3), which comprises culturing the transformant of above (8) in a medium to thereby produce and accumulate the polypeptide of any one of above (1) to (3) in the culture, and recovering the polypeptide from the culture.
(16) A process for producing a saccharide having the dihydroxyacetone moiety of the ketose transferred into the aldose, which comprises allowing a ketose and an aldose in an aqueous medium to coexist with an enzyme source selected from cells of the transformant of above (8) or (9), a culture of the transformant or a processed product of the culture, to thereby produce and accumulate the saccharide in the aqueous medium, and recovering the saccharide from the aqueous medium.

The invention is described in detail hereinafter.

(1) Polypeptide of the Present Invention:

The polypeptide of the present invention has the amino acid sequence of SEQ ID NO: 1. Polypeptides having the amino acid sequence of SEQ ID NO: 1 in which one or more amino acids have been substituted, deleted or added, and having transaldolase activity is within the scope of the polypeptide of the present invention.

The polypeptide having the amino acid sequence which has been substituted, deleted or added, and having transaldolase activity can be obtained according to the site-specific mutation method described in *Molecular Cloning, A Laboratory Manual*, Second Edition, Cold Spring Harbor Laboratory Press (1989) (hereinafter referred to as *Molecular Cloning*, 2nd Ed.), *Current Protocols in Molecular Biology*, John Wiley & Sons (1987–1997) (hereinafter referred to as *Current Protocols in Molecular Biology*), *Nucleic Acids Research*, 10, 6487 (1982), *Proc. Natl. Acad. Sci. USA*, 79, 6409 (1982), *Gene*, 34, 315 (1985), *Nucleic Acids Research*, 13, 4431 (1985), *Proc. Natl, Acad. Sci. USA*, 82, 488 (1985); for example, by introducing site-specific mutation into the DNA, that codes for a polypeptide having the amino acid sequence of SEQ ID NO: 1.

The number of amino acids to be deleted, substituted or added is not specifically defined, but preferably from 1 to tens of amino acids, more preferably from 1 to a few amino acids are deleted, substituted or added. In order that the polypeptide of the present invention has transaldolase activity, it is desirable that its amino acid sequence is at least 60%, generally at least 80%, especially at least 95% homologous to the amino acid sequence of SEQ ID NO: 1.

However, the polypeptide of the present invention does not include known polypeptides having transaldolase activity.

(2). DNA of the Present Invention:

The DNA of the present invention is a DNA which codes for the polypeptide of the present invention. For example, the DNA of the present invention has the nucleotide sequence of SEQ ID NO: 2.

DNAs that hybridize with the DNA of SEQ ID NO: 2 under stringent conditions are within the scope of the DNA of the present invention. The DNAs which hybridize with the DNA of SEQ ID NO: 2 under stringent conditions mean that it can be obtained through colony hybridization, plaque hybridization or southern hybridization using the DNA having the nucleotide sequence of SEQ ID NO: 2 or the internal fragment of the DNA as a probe. A specific example includes a DNA which can be identified through hybridization at 65° C. on a filter on which a colony or plaque-derived DNA or its fragment is fixed, in the presence of from 0.7 to 1.0 mol/liter of NaCl, followed by washing the filter at 65° C. with an SSC solution of about 0.1 to 2-fold concentration (the SSC solution of 0.1-fold concentration comprises 150 mmol/l of sodium chloride and 15 mmol/l of sodium citrate).

The hybridization may be conducted according to the method described in, for example, the laboratory manual, *Molecular Cloning*, 2nd Ed. Specifically, the hybridizable DNA is, for example, a DNA having the nucleotide sequence which is at least 80%, preferably at least 95% homologous to the nucleotide sequence of SEQ ID NO: 2.

However, the DNA of the present invention does not include known DNAs that code for polypeptides having transaldolase activity.

The DNA of the present invention can be isolated from the chromosomal DNA of a microorganism that belongs to the genus *Corynebacterium*, according to the method mentioned hereinafter. As for the gene source, any microorganism belonging to the genus *Corynebacterium* can be used so long as it belongs to the genus *Corynebacterium* or *Brevibacterium*. Specific examples of such

| | |
|---|---|
| Corynebacterium glutamicum | ATCC 31833 |
| Corynebacterium glutamicum | ATCC 13032 |
| Corynebacterium acetoacidophilum | ATCC 13870 |
| Corynebacterium callunae | ATCC 15991 |
| Corynebacterium herculis | ATCC 13868 |
| Corynebacterium mellacecola | ATCC 17965 |
| Corynebacterium lilium | ATCC 15990 |
| Corynebacterium ammoniagenes | ATCC 6872 |
| Brevibacterium immariophilum | ATCC 14068 |
| Brevibacterium saccharolyticum | ATCC 14066 |
| Brevibacterium thiogenitalis | ATCC 19240 |
| Brevibacterium divaricutum | ATCC 14020 |
| Brevibacterium flavum | ATCC 14067 |
| Brevibacterium lactofermentum | ATCC 13869 |

The chromosomal DNA of a microorganism belonging to genus *Corynebacterium* is extracted by using its culture, according to an ordinary method (for example, according to the method described in Japanese Published Unexamined Patent Application No. 126789/1983). The isolation of the DNA of the present invention from the chromosomal DNA comprises selecting a DNA which can complement the transketolase-deficient mutant [*Appl. Microboiol. Biotechnol.*, 50, 375 (1998)] obtained as a shikimic acid-requiring mutant.

Specifically, the chromosomal DNA is cleaved with suitable restriction enzymes and ligated with a vector plasmid, then a transketolase gene-deficient mutant [e.g., *Corynebacterium glutamicum* TKT6 (FERM BP-6399)] is transformed with the resulting plasmid, and the transformant having recovered the requirement for shikimic acid is selected. By selecting the plasmid carried by the transformant, the DNA of the present invention can be obtained along with a transketolase gene.

After the DNA of the present invention having the nucleotide sequence of SEQ ID NO: 2 is obtained, and the nucleotide sequence of the DNA is determined, primers are prepared based on the 5'-terminal nucleotide sequence and the 3'-terminal nucleotide sequence of the DNA. By using the chromosomal DNA obtained from a microorganism belonging to the genus *Corynebacterium* as a template along with the primer, PCR [PCR Protocols, Academic Press (1990)] is conducted to amplify a DNA to obtain the DNA of the present invention from other microorganism belonging to the genus *Corynebacterium*.

The DNA of the present invention can also be obtained from other microorganisms belonging to the genus *Corynebacterium* through colony hybridization or plaque hybridization (*Molecular Cloning*, 2nd Ed.) with chromosomal DNA prepared from a microorganism belonging to the genus *Corynebacterium*, wherein the full length or a part of the DNA of SEQ ID NO: 2 is used as a probe.

Furthermore, based on the nucleotide sequence represented by SEQ ID NO: 2, the DNA of the present invention can also be obtained through chemical synthesis with a Parkin Elmer's DNA synthesizer using phosphoamidation method.

(3) Production of Polypeptide of the Present Invention:

The polypeptide of the present invention can be produced according to the method described in *Molecular Cloning*, 2nd Ed. or *Current Protocols in Molecular Biology*, for example, by expressing the DNA of the present invention in host cells in the manner mentioned below.

A DNA fragment containing the part that codes for the polypeptide and having a suitable length is prepared. If desired, the nucleotide sequence coding for the polypeptide of the present invention is partly substituted with other nucleotides so as to be a codon most suitable for expression of the resulting DNA in host cells. The DNA is useful in efficient production of the polypeptide of the present invention.

The DNA fragment is inserted into the downstream site of the promoter of a suitable expression vector to construct a recombinant vector.

The recombinant vector is introduced into host cells suitable to the expression vector.

As a host cell, any cell can be used as long as it can express the intended gene, including bacteria, yeast cells, animal cells, insect cells and plant cells.

The expression vector shall be self-replicable in host cells or integrable with the chromosome therein, and shall have a promoter in the site in which the DNA coding for the polypeptide of the present invention can be transcribed.

In case where prokaryotes such as bacteria are used for host cells, it is desirable that the recombinant vector containing the DNA coding for the polypeptide of the present invention is self-replicable in prokaryotes and comprises a promoter, a ribosome-binding sequence, the DNA of the present invention and a transcription termination sequence. If desired, the recombinant vector may contain a promoter control gene.

The expression vector includes, for example, pBTrp2, pBTac1, pBTac2 (all commercial products of Boehringer Mannheim), pKK233-2 (produced by Pharmacia), pSE280 (produced by Invitrogen), pGEMEX-1 (produced by Promega), pQE-8 (produced by QIAGEN), pKYP10 (Japanese Published Unexamined Patent Application No. 110600/1983), pKYP200 [*Agric. Biol. Chem.*, 48, 669 (1984)], pLSA1 [*Agric. Biol. Chem.*, 53, 277 (1989)], pGEL1 [*Proc. Natl. Acad. Sci. USA*, 82, 4306 (1985)], pBluescript II SK(−) (by Stratagene), pTrs30 [prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM B-400), Japanese Published Unexamined Patent Application No. 221091/1985], pGKA2 [prepared from *Escherichia coli* IGKA2 (FERM BP-6798), Japanese Published Unexamined Patent Application No. 221091/1985], pTerm2 (U.S. Pat. Nos. 4,686,191, 4,939,094, and 5,160,735), pSupex, pUB110, pTP5, pC194, pEG400 [*J. Bacteriol.*, 172, 2392 (1990)], pGEX (produced by Pharmacia), and pET system (produced by Novagen).

Any promoter may be used, so long as it is capable of functioning in the host cells. For example, it is derived from *Escherichia coli* or phages, including trp promoter ($P_{trp}$), lac promoter, $P_L$ promoter, $P_R$ promoter and T7 promoter. Artificially-designed or modified promoters, such as $P_{trp} \times 2$ having two promoters in tandem, lacT7 promoter, and letI promoter.

A plasmid in which the distance between a Shine-Dalgarno sequence and an initiation codon is adjusted to an appropriate distance (e.g. 6 to 18 nucleotides) may be preferably used.

In the present invention, the recombinant vector does not always require a transcription termination sequence for expression of the DNA of the present invention. In the recombinant vector, however, it is desirable that a transcription termination sequence is just downstream the structural gene.

The host cells include microorganisms belonging to the genus *Escherichia*, *Serratia*, *Bacillus*, *Brevibacterium*, *Corynebacterium*, *Microbacterium* or *Pseudomonas*, including, for example, *Escherichia coli* XL 1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* G1698, *Escherichia coli* TB1, *Serratia ficaria*, *Serratia fonticola*, *Serratia liquefaciens*, *Serratia marcescens*, *Bacillus subtilis*, *Bacillus amyloliquefaciens*, *Brevibacterium ammoniagenes*, *Brevibacterium immariophilum* ATCC 14068, *Brevibacterium saccharolyticum* ATCC 14066, *Brevibacterium flavum* ATCC 14067, *Brevibacterium lactofermentum* ATCC 13869, *Corynebacterium glutamicum* ATCC 13032, *Corynebacterium glutamicum* ATCC 13869, *Corynebacterium acetoacidophilum* ATCC 13870, *Microbacterium ammoniaphilum* ATCC 15354, *Pseudomonas putida* and *Pseudomonas* sp. D-0110.

For introducing the recombinant vector into the host cells, any method of introducing DNA thereinto can be used, including the method by using calcium ions [*Proc. Natl. Acad. Sci. USA*, 69, 2110 (1972)], the protoplast method (Japanese Published Unexamined Patent Application No. 2483942/1988), and the methods described in *Gene*, 17, 107 (1982) and *Molecular &General Genetics*, 168, 111 (1979).

In case where yeast is used for host cells, the recombinant vector to be used in the case includes, for example, YEP13 (ATCC 37115), YEp24 (ATCC 37051), YCp50 (ATCC 37419), pHS19 and pHS15.

Any promoter may be used so long as it is capable of working in yeast cells, including, for example, promoters of genes participating in glycolysis such as hexose-kinase, as well as PH05 promoter, PGK promoter, GAP promoter, ADH promoter, gal 1 promoter, gal 10 promoter, heat-shock polypeptide promoter, MF α1 promoter, and CUP 1 promoter.

The host cells include microorganisms belonging to the genus *Saccharomyces*, *Schizosaccharomyces*, *Kluyveromyces*, *Trichosporon*, *Schwanniomyces*, *Pichia* and *Candida*, including, for example, *Saccharomyces cerevisiae*, *Schizosaccharomyces pombe*, *Kluyveromyces lactis*, *Trichosporon pullulans*, *Schwanniomyces alluvius* and *Candida utilis*.

For introducing the recombinant vector into the host cells, any method of introducing DNA into yeast cells can be used. For example, the electroporation method [*Methods Enzymol.*, 194, 182 (1990)], the spheroplast method [*Proc. Natl. Acad. Sci. USA*, 75, 1929 (1978)], the lithium acetate method [*J. Bacteriology*, 153, 163 (1983)], the method described in *Proc. Natl. Acad. Sci. USA*, 75, 1929 (1978) and the like, can be mentioned.

In case where animal cells are used for host cells, the expression vector to be used in the case includes, for example, pcDNAI, pcDM8 (produced by Funakoshi), pAGE107 [Japanese Published Unexamined Patent Application No. 22979/1991, *Cytotechnology*, 3, 133 (1990)], pAS3—3 (Japanese Published Unexamined Patent Application No. 227075/1990), pCDM8 [*Nature*, 329, 840 (1987)], pcDNAI/Amp (produced by Invitrogen), pREP4 (produced by Invitrogen), pAGE103 [*J. Biochem.*, 101, 1307 (1987)], and pAGE210.

Any promoter may be used as long as it is capable of functioning in animal cells, including, for example, the promoter of IE (immediate early) gene of cytomegalovirus (CMV), the early promoter of SV40 and the promoter of retrovirus, as well as metallothionein promoter, heat-shock promoter, and SRα promoter. The enhancer of the IE gene of human CMV may be used together with the promoter.

The host cells include, for example, Namalwa cells that are human cells, COS cells that are monkey cells, CHO cells and HBT5637 cells that are Chinese hamster cells (Japanese Published Unexamined Patent Application No. 299/1988).

For introducing the recombinant vector into the animal cells, any method of introducing DNA into animal cells can be used. For example, the electroporation method [*Cytotechnology*, 3, 133 (1990)], the calcium phosphate method (Japanese Published Unexamined Patent Application No. 227075/1990), the lipofection method [*Proc. Natl. Acad. Sci. USA*, 84, 7413 (1987)], the method described in *Virology*, 52, 456 (1973) and the like, can be mentioned.

In case where insect cells are used for host cells, polypeptide may be expressed, for example, according to the methods described in *Current Protocols in Molecular Biology; Baculovirus Expression Vectors*, A Laboratory Manual, W. H. Freeman and Company, New York (1992); and *Bio/Technology*, 6, 47 (1988).

That is, a recombinant gene-introduction vector and a Baculovirus are simultaneously introduced into insect cells to form a recombinant virus in the supernatant of the insect cell culture, and then insect cells are infected with the recombinant virus so as to express the polypeptide.

The gene-introduction vector to be used in the method includes, for example, pVL1392, pVL1393 and pBlueBacIII (all produced by Invitrogen).

The Baculovirus is, for example, *Autographa californica* nuclear polyhedrosis virus that infects insects of the family Barathra.

The insect cells include, for example, *Spodopetera frugiperda* oocytes, Sf9, Sf21 [*Baculovirus Expression Vectors*, A Laboratory Manual, W. H. Freeman and company, New York (1992)], and *Trichoplusia ni* oocytes, High 5 (produced by Invitrogen).

For the simultaneously introduction of the recombinant gene-introduction vector and the Baculovirus into insect cells to prepare the recombinant virus, for example, a calcium phosphate method (Japanese Published Unexamined Patent Application No. 227075/1990), the lipofection method [*Proc. Natl. Acad. Sci. USA*, 84, 7413 (1987)] and the like, can be mentioned.

In case where plant cells are used for host cells, the expression vector includes, for example, Ti plasmid and tobacco mosaic virus vector.

Any promoter may be used, so long as it is capable of being expressed in plant cells, including, for example, 35S promoter of cauliflower mosaic virus (CaMV), and rice actin 1 promoter.

The plant cells for host cells include, for example, those of tobacco, potato, tomato, carrot, soybean, rape, alfalfa, rice, wheat, and barley.

For introducing the recombinant vector into such plant cells, any method of introducing DNA thereinto, including, for example, the method of introducing it into *Agrobacterium* (Japanese Published Unexamined Patent Application No. 140885/1984 and 70080/1985, WO94/00977), the electroporation method (Japanese Published Unexamined Patent Application No. 251887/1985), and the method by using a particle gun (gene gun) (Japanese Patent No. 2,606,856, 2,517,813) can be mentioned.

The gene expression may be conducted in a mode of direct expression, or alternatively, in a mode of secretion production or fused protein expression according to the method described in *Molecular Cloning*, 2nd Ed.

In case where the gene is expressed in yeast cells, animal cells, insect cells or plant cells, it gives a polypeptide with a saccharide or sugar chain added thereto.

The transformant of the present invention prepared in the manner as above is cultured in a medium, and the polypeptide of the present invention is produced and accumulated in the culture, and recovered from the culture.

For culturing the transformant of the present invention in a medium, any method as conventionally used for host cultivation in the art can be used.

In case where the transformant of the present invention is prepared by the use of prokaryotic cells such as *Escherichia coli* or eukaryotic cells such as yeast as a host cell, the medium in which the transformant is cultured may be any natural or synthetic medium containing carbon sources, nitrogen sources and inorganic salts which can be assimilated by the transformant and in which the transformant can be efficiently cultured.

The carbon sources may be any ones which can be assimilated by the transformant, including, for example, carbohydrates such as glucose, fructose, sucrose, molasses containing them, starch or starch hydrolyzates; organic acids such as acetic acid, propionic acid and the like; and alcohols such as ethanol, propanol and the like.

The nitrogen sources include, for example, ammonia, ammonium salts of various inorganic acids and organic acids, such as ammonium chloride, ammonium sulfate, ammonium acetate, ammonium phosphate; other nitrogen-containing compounds; and peptone, meat extracts, yeast extracts, corn steep liquor, casein hydrolyzates, soy bean meal, soy bean meal hydrolyzates, various cells obtained by fermentation and their digested products.

The inorganic salts include, for example, potassium dihydrogenphosphate, dipotassium hydrogenphosphate, magnesium phosphate, magnesium sulfate, sodium chloride, ferrous sulfate, manganese sulfate, copper sulfate, and calcium carbonate.

Culturing the transformant in the medium is conducted under aerobic conditions, for example, in a mode of shaking culture or deep aeration stirring culture. The culturing temperature is preferably from 15 to 40° C., and the culturing period is generally from 16 hours to 7 days. Preferably, the pH of the culture is from 3.0 to 9.0. For the pH control, any of inorganic or organic acids, alkali solutions, urea, calcium carbonate, ammonia or the like can be used.

If desired, antibiotics such as ampicillin and tetracycline may be added to the medium in which the transformant is cultured.

In case where microorganisms transformed with a recombinant vector having an inductive promoter are cultured, an inducer may be added to the medium, if desired. For example, when microorganisms transformed with a recombinant vector having lac promoter are cultured, isopropyl-β-D-thiogalactopyranoside may be added to the medium; and when microorganisms transformed with a recombinant vector having trp promoter are cultured, indole-acrylic acid may be added to the medium.

The medium in which the transformant prepared by the use of animal cells as a host cell is cultured may be any ordinary one, including, for example, RPMI1640 medium [*The Journal of the American Medical Association*, 199, 519 (1967)], Eagle's MEM medium [*Science*, 122, 501 (1952)], Dulbecco's modified MEM medium [*Virology*, 8, 396 (1959)], 199 medium [*Proceeding of the Society for the Biological Medicine*, 73, 1 (1950)], and those media with fetal calf serum therein.

Culturing the transformant in the medium is conducted generally at pH of from 6 to 8, at 30 to 40° C. in the presence of 5% $CO_2$ for 1 to 7 days.

If desired, antibiotics such as kanamycin and penicillin may be added to the medium in which the transformant is cultured.

The medium in which the transformant prepared by the use of insect cells as a host cell is cultured may be any ordinary one, including, for example, TNM-FH medium (produced by PharMingen), Sf-900 II SFM medium (produced by Life Technologies), ExCell 400 and ExCell 405 [both produced by JRH Biosciences], Grace's Insect Medium [*Nature*, 195, 788 (1962)].

Culturing the transformant in the medium is conducted generally at pH of from 6 to 7, at 25 to 30° C. for 1 to 5 days.

If desired, antibiotics such as gentamycin may be added to the medium in which the transformant is cultured.

The transformant cells prepared by the use of plant cells as a host cell may be cultured as they are, or after differentiated into plant cells or organs. The medium in which the transformant is cultured may be any ordinary one, including, for example, Murashige & Skoog (MS) medium, White medium, and those media with a plant hormone such as auxin or cytokinin therein.

Culturing the transformant in the medium is conducted generally at pH of from 5 to 9, at 20 to 40° C. for 3 to 60 days.

If desired, antibiotics such as kanamycin and hygromycin may be added to the medium in which the transformant is cultured.

As described above, the transformant derived from microorganisms, animal cells or plant cells carrying a recombinant vector ligated with the DNA coding for the polypeptide of the present invention is recovered according to conventional method to thereby produce and accumulate the polypeptide, and the polypeptide is recovered from the culture.

The gene expression may be conducted in a mode of direct expression, or in a mode of secretion production or fused polypeptide expression according to the method described in *Molecular Cloning*, 2nd Ed.

The method of producing the polypeptide of the present invention includes intracellular production, extracellular secretion and production on outer membrane of host cells. The method can be selected depending on the host cells used or on alternation of the structure of the polypeptide to be produced.

In case where the polypeptide of the present invention is produced inside host cells or on the outer membrane of host cells, it can be positively secreted to the extracellular portion from the host cells, according to the method of Paulson, et al. [*J. Biol. Chem.*, 264, 17619 (1989)], the method of Lowe, et al. [*Proc. Natl. Acad. Sci., USA*, 86, 8227 (1989), *Genes Develop.*, 4, 1288 (1990)] or the methods described in Japanese Published Unexamined Patent Application No. 336963/1993 and WO94/23021.

That is, the polypeptide of the present invention can be positively secreted in the extracellular portion from the host cells, by expressing it in the form of a polypeptide containing the active site of the polypeptide of the present invention and having a signal peptide upstream it, according to the genetic recombinant technology.

The yield of the polypeptide to be produced can be increased in a gene amplification system using a dihydrofolate reductase gene or the like, according to the method described in Japanese Published Unexamined Patent Application No. 227075/1990.

In addition, the gene-introduced animal or plant cells may be re-differentiated to construct gene-introduced animal individuals (transgenic non-human animals) or plant individuals (transgenic plants). Using these individuals, the polypeptide of the present invention may be produced.

In case where the transformant is an animal individual or plant individual, it may be raised or cultivated according to a conventional method to thereby produce and accumulate the intended polypeptide therein, and the polypeptide is recovered from the animal or plant individual.

For producing the polypeptide of the present invention in animal individuals, for example, an animal is transformed with the gene of the present invention introduced thereinto and the polypeptide is produced in the transformant animal according to known methods [*American Journal of Clinical Nutrition*, 63, 639S (1996), *American Journal of Clinical Nutrition*, 63, 627S (1996), *Bio/Technology*, 9, 830 (1991)].

For animal individuals, for example, the transgenic non-human animals carrying the DNA coding for the polypeptide of the present invention are raised to thereby produce and accumulate the polypeptide in the animals, and the polypeptide is recovered from the animals. The site of the animals in which the polypeptide is produced and accumulated is, for example, milk (Japanese Published Unexamined Patent Application No. 309192/1988, eggs of the animals, and the like. Any promoter may be used so long as it is capable of being expressed in animals. Its preferred examples are mammary gland cell-specific promoters such as α-casein promoter, β-casein promoter, β-lactoglobulin promoter, whey acidic protein promoter, and the like.

For producing the polypeptide of the present invention in plant individuals, for example, a transgenic plant carrying the DNA coding for the polypeptide of the present invention is cultivated according to known methods [*Tissue Culture*, 20 (1994), *Tissue Culture*, 21 (1995), *Trends in Biotechnology*, 15, 45 (1997)] to thereby produce and accumulate the polypeptide in the plant, and the polypeptide is recovered from the plant.

For isolating and purifying the polypeptide produced by the transformant of the present invention, any conventional method for enzyme isolation and purification can be used. For example, when the polypeptide of the present invention is expressed in soluble forms inside the transformant cells, the cells are cultured, recovered from the culture by centrifuging the culture, then suspended in an aqueous buffer, and disrupted with an ultrasonic disrupter, French Press, Manton-Gaulin homogenizer, Dynomill or the like to obtain a cell-free extract. The cell-free extract is centrifuged, and the resulting supernatant is purified through conventional enzyme isolation and purification. Specifically, for example, the supernatant is purified through solvent extraction, salting-out or desalting with sulfate ammonium or the like, precipitation with organic solvent, anion-exchange chromatography on resin such as diethylaminoethyl (DEAE)-Sepharose or DIAION HPA-75 (produced by Mitsubishi Chemical Industries), or the like, cation-exchange chromatography on resin such as S-Sepharose FF (produced by Pharmacia) or the like, hydrophobic chromatography on resin such as butyl Sepharose or phenyl Sepharose, gel filtration through molecular sieve, affinity chromatography, chromatofocusing, or electrophoresis such as isoelectric focusing, or the like. The purification methods may be used either singly or as combined to obtain the intended pure product.

In case where the polypeptide is expressed as an inclusion body in the cells, the cells are similarly recovered, disrupted and centrifuged to give a precipitated fraction as the inclusion body including the polypeptide of the present invention. The thus-recovered insoluble polypeptide is solubilized with a protein denaturing agent. The solubilized solution is then diluted or dialyzed to thereby lower the concentration of the protein denaturing agent in the solution. Through the process, the solubilized polypeptide is renatured to have its own normal tertiary structure. After thus processed, a pure product of the polypeptide is obtained through the same isolation and purification methods as in the above.

In case where the polypeptide of the present invention or the polypeptide derivative with a sugar chain added thereto is secreted outside from the cells, the polypeptide or the polypeptide derivative can be recovered in the culture supernatant. Specifically, the culture is centrifuged in the same manner as above to obtain the culture supernatant, and then a pure product of the polypeptide is obtained through the same isolation and purification methods as in the above from the culture supernatant.

The polypeptide thus obtained in the manner as above is, for example, the polypeptide having the amino acid sequence of SEQ ID NO: 1.

The polypeptide of the present invention can be produced through chemical synthesis of, for example, the Fmoc method (fluorenylmethyloxycarbonyl method) or the tBoc method (b-butyloxycarbonyl method). It may also be produced through chemical synthesis using peptide synthesizers such as those produced by Advanced ChemTech, Parkin-Elmer, Pharmacia, Protein Technology Instrument, Synthecell-Vega, PerSeptive, and Shimadzu.

(4) Method for Producing Substances Using the DNA of the Present Invention:

(a) Production of Aromatic Compounds Such as Aromatic Amino Acids and Aromatic Vitamins; Nucleic Acid-Associated Substances Such as Purine-Nucleotide and Pyrimidine-Nucleotide; and L-Histidine and Riboflavin:

Using the DNA of the present invention or based on its nucleotide sequence information, the transaldolase activity of the transformants having an ability to produce aromatic compounds such as aromatic amino acids and aromatic vitamins, nucleic acid-associated substances such as purine-nucleotide and pyrimidine-nucleotide, and L-histidine and riboflavin can be modified in any desired manner, and industrial methods for producing their metabolites can be thereby provided.

The aromatic amino acids capable of being obtained in the invention include, for example, phenylalanine, tyrosine and tryptophan; the aromatic vitamins include, for example, folic acid (vitamin M), menaquinone (vitamin K2), p-hydroxybenzoic acid and ubiquinone derived from it, p-aminobenzoic acid (vitamin H'), anthranilic acid (vitamin L), tocopherol (vitamin E); and the nucleic acid-associated substances include, for example, purine-nucleotide, pyrimidine-nucleotide, purine-nucleoside, pyrimidine-nucleoside, purine base, pyrimidine base and flavin-nucleotide.

Methods for producing these substances are described below.

In the transformants prepared in the above (3), the DNA of the present invention or a DNA existing upstream the DNA of the present invention and participating the transcription and translation of the DNA is modified such that one or more nucleotides are deleted, substituted or added in its nucleotide sequence to thereby construct transformants that carry the thus-modified DNA (these are hereinunder referred to as transformant variants). From the transformant variants, transformant variants having enhanced transaldolase activity, or those having reduced or no transaldolase activity are selected. The nucleotides deletion, substitution and addition may be conducted in the known method (for example, described in *Molecular Cloning*, 2nd Ed., *Current Protocols in Molecular Biology*).

The transaldolase activity can be measured according to the process of Example (4) mentioned hereinafter.

That is, each transformant variant is cultured according to the method of above (3) to prepare a crude enzyme solution. The crude enzyme solution is added to a reaction solution [containing 40 mmol/l Tris (pH 7.6), 0.1 mmol/l diphosphopyridine, 2.8 mmol/l fructose 6-phosphate, 0.2 mmol/l erythrose 4-phosphate, 10 $\mu$g of glycerol 3-phosphate dehydrogenase and triose phosphate isomerase mixture (produced by Boehringer Mannheim)] to make 1 ml, and the reaction is carried out at 25° C. The enzymatic activity of the transformant variant can be measured, by measuring the reduction in the absorbance at 340 nm of the reaction mixture with a spectrophotometer to determine the amount of glyceraldehyde 3-phosphate produced in the reaction mixture.

According to the method as above, the transaldolase activity of transformant variants is measured, and the intended transformant variants having increased, reduced or lost transaldolase activity can be selected from all the transformant variants.

When using cells which can produce aromatic amino acids or aromatic vitamins as a host cell, their ability to produce the intended aromatic compounds can be increased, by increasing their transaldolase activity.

When using cells which can produce nucleic acid-associated substances such as purine-nucleotide and pyrimidine-nucleotide, L-histidine or riboflavin as a host cell, their ability to produce the substances can be increased, by lowering or deleting their transaldolase activity.

The transformant obtained in the manner as above is cultured in a medium to thereby produce and accumulate the intended product of aromatic amino acids, aromatic vitamins, L-histidine, riboflavin, purine-nucleotide, pyrimidine-nucleotide and other nucleic acid-associated substances, in the culture, and the product is isolated and purified from the culture according to known methods including concentration crystallization, activated charcoal treatment and ion-exchange resin treatment [Isao Endo et al's Bioseparation Process Handbook, edited by the Chemical Engineering Society of Japan, published by Kyoritsu Publishing (1996)]. Through the process, the intended substance can be obtained efficiently.

Culturing the transformant may be conducted in the same manner as in the above (3) that indicates the method for culturing transformants for producing the polypeptide of the present invention.

(b) Production of Novel Saccharides:

A ketose and an aldose are allowed to exist in an aqueous medium containing, as an enzyme source, the transformant obtained according to the method mentioned above, a culture of the transformant or a processed product of the culture, to thereby produce and accumulate in the aqueous medium a saccharide having the dihydroxyacetone moiety of the ketose transferred into the aldose owing to the transaldolase activity of the enzyme source, and the saccharide is recovered from the aqueous medium.

The ketose includes, for example, sedoheptulose 7-phosphate, fructose 6-phosphate and the like; and the aldose includes, for example, erythrose 4-phosphate, glyceraldehyde 3-phosphate and the like.

The processed product of the transformant culture includes, for example, cultured cells; processed cells such as dried cells, lyophilized cells, surfactant-processed cells, enzyme-processed cells, ultrasonically-processed cells, mechanically disrupted cells, solvent-processed cells; as well as enzyme products extracted from cultured cells, such as protein fractions of cultured cells, and immobilized products of cultured cells and processed cells.

The concentration of the enzyme source to be used in producing the saccharides of the present invention may be from 1 mU/liter to 1,000 U/liter, preferably from 10 mU/liter to 100 U/liter. One unit (U) is meant to indicate the activity of the enzyme source that produces 1 mmol of the saccharide at 37° C. for 1 minute.

The aqueous medium to be used in producing the saccharides of the present invention includes, for example, water; buffers such as phosphates, carbonates, acetates, borates, citrates, Tris, or the like; alcohols such as methanol, ethanol, or the like; esters such as ethyl acetate, or the like; ketones such as acetone, or the like; and amides such as acetamide, or the like. The culture of the transformant serving as the enzyme source may also be used for the aqueous medium.

If desired, surfactant and organic solvent may be added to the system of producing the saccharides of the present invention. Any surfactant may be used so long as it is capable of promoting the production of galactose-containing saccharides, including, for example, nonionic surfactants such as polyoxyethylene-octadecylamine (e.g., Naimeen S-215 produced by Nippon Yushi); cationic surfactants such as cetyltrimethylammonium bromide and alkyldimethylbenzylammonium chlorides (e.g., Cation F2-40E produced by Nippon Yushi); anionic surfactants such as lauroyl sarcosinate; and tertiary amines such as alkyldimethylamines (e.g., Tertiary Amine FB, produced by Nippon Yushi). One or more such surfactants may be used either singly or as combined. The surfactant concentration is usually from 0.1 to 50 g/l. The organic solvent includes, for example, xylene, toluene, aliphatic alcohols, acetone, and ethyl acetate. The solvent concentration is usually from 0.1 to 50 ml/liter.

The quantification of the saccharide formed in the aqueous medium according to the invention can be conducted, for example, with a Dionex's saccharide analyzer [*Anal. Biochem.*, 189, 151 (1990)].

The saccharides formed in the reaction mixture according to the present invention can be recovered by a conventional method, using activated charcoal or ion-exchange resin, or the like.

The method of the present invention makes it easy to produce saccharides which have heretofore been difficult to produce, and makes it possible to produce novel saccharides.

Examples of the present invention are described below, to which, however, the invention is not limited.

BEST MODES FOR CARRYING OUT THE INVENTION (1) Acquisition of a Transketolase-Deficient Mutant of *Corynebacterium glutamicum*:

*Corynebacterium glutamicum* L22 [a lysozyme-sensitive mutant derived from a wild type strain ATCC 31833; R. Katsumata et al., *Proc. 4th Eur. Congr. Biotechnol.*, 4, 767 (1987)] was inoculated in 3 ml of NB medium [containing 20 g of bouillon powder and 5 g of yeast extract in water 1 liter and having pH 7.2] and cultured therein at 30° C. until $OD_{660}$ of the culture reached to 0.6.

After culturing, the cells were recovered through centrifugation, and washed once with 50 mmol/l Tris maleate buffer (pH 6.0), and subjected to a mutational treatment in 3 ml of the buffer containing 400 mg/l of NTG, at room temperature for 20 minutes. The treated cells were centrifuged and washed twice with the buffer, and then cultured in 3 ml of NB medium at 30° C. for 1 hour.

The culture was diluted with physiological saline to $10^{-5}$ to $10^{-6}$, and 0.1 ml of the resulting dilution was spread on NB-agar medium [NB medium with 1.4% agar, pH 7.2], and cultured thereon at 30° C. for 2 days.

Each of the colonies grown on the agar medium were spread on minimal agar medium M1 [containing 10 g of glucose, 1 g of $(NH_4)H_2PO_4$, 0.2 g of KCl, 0.2 g of $MgSO_4.7H_2O$, 10 mg of $FeSO_4.7H_2O$, 0.2 mg of $MnSO_4.4–6H_2O$, 0.9 mg of $ZnSO_4.7H_2O$, 0.4 mg of $CuSO_4.5H_2O$, 0.09 mg of $Na_2B_4O_7.10H_2O$, 0.04 mg of $(NH_4)_6Mo_7O_{24}.4H_2O$, 50 mg of biotin, 2.5 mg of p-aminobenzoic acid, 1 mg of thiamin hydrochloride and 16 g of agar in water 1 liter, and adjusted pH 7.2] and on M1 agar medium containing 50 mg/l shikimic acid, and cultured thereon at 30° C.

The colonies grown on the M1-agar medium containing 50 mg/l of shikimic acid, but not growing on the minimal agar medium M1 were separated as shikimic acid-requiring mutants. The thus-separated shikimic acid-requiring mutant were spread on M1-agar-medium containing 50 mg/l of shikimic acid and onto the medium in which the glucose was substituted with ribose, and cultured thereon at 30° C.

The shikimic acid-requiring mutant grown on the M1-agar medium containing 50 mg/l of shikimic acid, but not growing on the medium containing ribose in place of glucose were separated as shikimic acid-requiring and ribose-non-assimilating mutants.

The thus-separated, shikimic acid-requiring and ribose-non-assimilating mutant cells were cultured in 40 ml of M1 medium containing 50 mg/l of shikimic acid, at 30° C. for 24 hours. The cells were collected through centrifugation, ultrasonically disrupted, and again centrifuged to prepare a cell-free extract. The transketolase activity of the cell-free extract was determined as follows, using the cell-free extract as a crude enzyme solution.

The crude enzyme solution was added to a reaction solution [containing 50 mmol/l Tris (pH7.5), 0.2 mmol/l NADH, 0.01 mmol/l thiamin pyrophosphate, 1 mmol/l $MgCl_2$, 0.5 mmol/l xylulose 5-phosphate, 0.5 mmol/l ribulose 5-phosphate, and 10 μg of a mixture of glycerol 3-phosphate dehydrogenase and triose phosphate isomerase (produced by Boehringer Mannheim)] to make 1.5 ml, and the reaction was carried out at 30° C.

The amount of glyceraldehyde 3-phosphate produced in the reaction mixture was determined by measuring the reduction in the absorbance at 340 nm of NADH in the reaction medium with spectrophotometer.

From the result of the measurement, a transketolase activity-deficient mutant TKT6, not being capable of producing glyceraldehyde 3-phosphate at all was selected, from the separated shikimic acid-requiring and ribose-non-assimilating mutants.

*Corynebacterium glutamicum* TKT6 has been deposited as FERM BP-6399 since Jun. 30, 1998 with the International Patent Organism Deopsitary National Institute of Advanced Industrial Science and Technology, Tsukuba Central 6, 1—1, Higashi 1-Chome Tsukuba-shi, Ibaraki-ken 305-8566 Japan (National Institute of Bioscience and Human-Technology, Agency of Industrial Science and Technology, 1-3, Higashi 1-chome, Tsukuba city, Ibaragi prefecture, 305-8566, Japan), under the Budapest Treaty.

(2) Cloning of DNA Fragments Containing Transketolase Gene and Transaldolase Gene:

For the source of the two genes, a chromosomal DNA of *Corynebacterium glutamicum* ATCC 31833 was used; and for the recipient of the genes, the transketolase gene-deficient *Corynebacterium glutamicum* TKT6 (FERM BP-6399) obtained in Example 1 was used. For the vector, a plasmid pCSEK20 replicable in *Corynebacterium glutamicum* was used. The plasmid pCSEK20 comprises a replication origin of plasmid pCG2 derived from *Corynebacterium glutamicum* (Japanese Published Unexamined Patent Application No. 35197/1983), a spectinomycin and streptomycin-resistant gene of plasmid pCG4 derived from *Corynebacterium glutamicum* (Japanese Published Unexamined Patent Application No. 183799/1982) and a kanamycin-resistant gene of an conventionally-using-vector pGA22 [*J. Bacteriol.*, 140, 400 (1979)] for *Escherichia coli* [*Appl. Microbiol. Biotechnol.*, 51, 201 (1999)].

Culturing of *Corynebacterium glutamicum* ATCC 31833 and preparation of the chromosomal DNA from the culture was conducted according to the method described in Japanese Published Unexamined Patent Application No. 169785/1994. Plasmid pCSEK20 was isolated from the cultured cells of *Corynebacterium glutamicum* ATCC 31833 carrying it, according to the vector preparation method described in Japanese Published Unexamined Patent Application No. 169785/1994.

The cloning of the fragment containing transketolase gene and transaldolase gene from the chromosomal DNA of *Corynebacterium glutamicum* ATCC 31833 was conducted as follows.

The chromosomal DNA and the pCSEK20 plasmid DNA prepared as in the above, 1 $\mu$g each, were cleaved with EcoRI (5 units), and their fragments were ligated with a ligation kit (produced by Takara Shuzo). Using the thus-constructed plasmid, the shikimic acid-requiring, transketolase gene-deficient *Corynebacterium glutamicum* TKT6 (FERM BP-6399) was transformed as follows.

*Corynebacterium glutamicum* TKT6 was inoculated in 5 ml of NB medium, and cultured therein at 30° C. for 1 day. The obtained seed culture (4 ml) was inoculated in 40 ml of SSM medium [containing 20 g of glucose, 10 g of $(NH_4)_2SO_4$, 3 g of urea, 1 g of yeast extract, 1 g of $KH_2PO_4$, 0.4 g of $MgCl_2.6H_2O$, 10 mg of $FeSO_4.7H_2O$, 0.2 mg of $MnSO_4.4–6H_2O$, 0.9 mg of $ZnSO_4.7H_2O$, 0.4 mg of $CuSO_4.5H_2O$, 0.09 mg of $Na_2B_4O_7.10H_2O$, 0.04 mg $(NH_4)_6Mo_7O_{24}.4H_2O$, 30 $\mu$g of biotin and 1 mg of thiamin hydrochloride in water 1 liter, and adjusted pH 7.2] containing 100 $\mu$g/ml shikimic acid, and cultured with shaking at 30° C. until $OD_{660}$ Of the culture reached to 0.6.

The cells were collected, and suspended in 10 ml of lysozyme-containing RCGP medium [containing 5 g of glucose, 5 g of casamino acid, 2.5 g of yeast extract, 1.5 g of $KH_2PO_4$, 0.41 g of $MgCl_2.6H_2O$, 10 mg of $FeSO_4.7H_2O$, 2 mg of $MnSO_4.4–6H_2O$, 0.9 mg of $ZnSO_4.7H_2O$, 0.04 mg of $(NH_4)_6Mo_7O_{24}.4H_2O$, 30 $\mu$g of biotin, 2 mg of thiamin hydrochloride, 135 g of disodium succinate and 30 g of polyvinylpyrrolidone (molecular weight 10,000) in water 1 liter] to have a cell concentration of about $10^9$ cells/ml. The cell suspension was transferred into an L-shaped test tube and reacted therein with gently stirring at 30° C. for 6 hours to obtain protoplast.

The thus-obtained 0.5 ml of the protoplast was put into a small test tube, centrifuged at 2,500×g for 5 minutes, re-suspended in 1 ml of TSMC buffer (10 mmol/l $MgCl_2$, 30 mmol/l $CaCl_2$, 50 mmol/l Tris, 400 mmol/l sucrose, pH 7.5), centrifuged and washed, and then re-suspended in 0.1 ml of TSMC buffer. The cell suspension was mixed with 100 $\mu$l of a 1/1 mixture of TSMC buffer of 2-fold concentration and the above-mentioned ligation mixture, followed by adding of 0.8 ml of 20% PEG (6,000)-containing TSMC buffer, and further mixed. After 3 minutes, 2 ml of RCGP medium (pH 7.2) was added to the mixture, and centrifuged at 2,500×g for 5 minutes to remove the supernatant. The precipitated protoplast was suspended in 1 ml of RCGP medium. The cell suspension (0.2 ml) was spread on RCGP-agar medium (1.4% agar-containing RCGP medium, pH 7.2) containing 200 $\mu$g/ml kanamycin, and cultured thereon at 30° C. for 10 days.

The colonies grown on the agar medium were scraped up, centrifuged and washed twice with physiological saline, and suspended in 1 ml of physiological saline. The cell suspension was again spread on minimal agar medium M1 [containing 10 g of glucose, 1 g of $(NH_4)H_2PO_4$, 0.2 g of KCl, 1 g of $KH_2PO_4$, 0.2 g of $MgSO_4.7H_2O$, 10 mg of $FeSO_4.7H_2O$, 0.2 mg of $MnSO_4.4–6H_2O$, 0.9 mg of $ZnSO_4.7H_2O$, 0.4 mg of $CuSO_4.5H_2O$, 0.09 mg of $Na_2B_4O_7.10H_2O$, 0.04 mg of $(NH_4)_6Mo_7O_{24}.4H_2O$, 50 $\mu$g of biotin, 2.5 mg of p-aminobenzoic acid, 1 mg of thiamin hydrochloride and 16 g of agar in water 1 liter, and adjusted pH 7.2] containing 20 $\mu$g/ml kanamycin, and cultured thereon at 30° C. for 3 days. Through the process, a kanamycin-resistant and shikimic acid-non-requiring transformant was selected.

From transformants, plasmid DNAs were isolated according to the vector preparation method described in Japanese Published Unexamined Patent Application No. 169785/1994. A plasmid was obtained from one strain of the transformant, and named pCTK60. DNA fragments cleaved with restriction enzymes were analyzed through agarose gel electrophoresis, which confirmed that the plasmid has a structure of about 7.6 kb EcoRI DNA fragment inserted into the EcoRI site of pCSEK20. Through subcloning and complementation test, it was found that at least a transketolase gene exist on about 4.1 kb XhoI-EcoRI DNA fragment contained in the EcoRI DNA fragment.

(3) Sequencing of XhoI-EcoRI DNA Fragment:

From the plasmid having approximately 4.1 kb XhoI-EcoRI DNA fragment, the DNA fragment was recovered according to a conventional method. The DNA fragment and a vector pUC19 (produced by Takara Shuzo) were cleaved with various restriction enzymes, and the vector DNA fragment was ligated with the decomposed DNA fragment by using a T4DNA ligase. *Escherichia coli* DH5α (produced by Toyobo) was transformed with the ligated mixture according to a conventional method. The resulting transformant cells were spread on LB-agar medium [containing 10 g of tryptone, 5 g of yeast extract, 10 g of NaCl and 20 g of agar dissolved in water 1 liter] containing ampicillin to a final concentration 100 $\mu$g/ml, and cultured thereon at 37° C. for 16 hours.

The strains grown on the selective medium were inoculated in LB medium containing ampicillin to a final concentration of 100 $\mu$g/ml, and cultured therein at 30° C. for 12 hours. From the cultured cells, a plasmid was isolated through alkali-SDS method (*Molecular Cloning*, 2nd Ed.).

By using the thus-isolated plasmid DNA, the nucleotide sequence of the DNA fragments inserted into the vector pUC19 was analyzed and determined, according to the dideoxynucleotide enzyme method. Specifically, the plasmid DNA was processed with Thermo Sequenace cycle sequencing kit (produced by Amersham) according to the protocol, and the inserted DNA fragments were sequenced with a DNA sequencer, LONG READER 4200 (by LI-COR). The nucleotide sequence of the inserted DNA fragments is shown by SEQ ID NO: 3.

The nucleotide sequence was analyzed with a sequence-analyzing soft, GENETYX MAC ATSQ 3.0 by Software Development.

As a result, it was found that two open reading frames exist in the nucleotide sequence of the 4.1 kb XhoI-EcoRI DNA fragment.

The primary structure of the amino acid sequence estimated from the nucleotide sequence of the DNA fragment was compared with that of the amino acid sequence of transketolase and transaldolase of *Mycobacterium tuberculosis* which is taxonomically similar to the genus *Corynebacterium*, and it was confirmed that the open reading frame existing at 373rd to 2472nd in the nucleotide sequence of SEQ ID NO: 3 is a transketolase gene, and the open reading frame existing at 2643rd to 3722nd is a transaldolase gene. The amino acid sequence estimated from the open reading frame of the transaldolase gene is shown by SEQ ID NO: 1; and the nucleotide sequence thereof is shown by SEQ ID NO:2.

(4) Determination of Transketolase Activity and Transaldolase Activity:

The XhoI-EcoRI DNA fragment of approximately 4.1 kb was, after its both ends had been repaired to be blunt according to the conventional method, inserted into the SmaI site of a vector pCG116 replicable in *Corynebacterium glutamicum* [*Appl. Microbiol. Biotechnol.*, 51, 201 (1999)] to construct a recombinant plasmid pHTK65. *Corynebacterium glutamicum* ATCC 31833 was transformed with the recombinant plasmid, and the transketolase and transaldolase activity of the transformant was measured. The transketolase activity of the transformant was measured according to the method described in Japanese Published Unexamined Patent Application No. 169785/1994; and the transaldolase activity thereof was measured as follows.

A crude enzyme solution was added to a reaction solution [containing 40 mmol/l Tris (pH7.6), 0.1 mmol/l diphosphopyridine, fructose 6-phosphate 2.8 mmol/l, 0.2 mmol/l erythrose 4-phosphate, 10 µg of a mixture of glycerol 3-phosphate dehydrogenase and triose phosphate isomerase mixture (produced by Boehringer Mannheim)] to make 1 ml, and the reaction was carried out at 25° C. The amount of glyceraldehyde 3-phosphate produced in the reaction mixture was quantified by measuring the reduction in the absorbance at 340 nm of the reaction medium by using a spectrophotometer. Both of the transketolase activity and the transaldolase activity of the pHTK65-carrying transformant increased at least 5 times more than those of ATCC31833, when those of ATCC 31833 per unit protein weight and unit time is defined to be one.

INDUSTRIAL APPLICABILITY

The novel transaldolase gene of the present invention and its nucleotide sequence information, as well as the polypeptide encoded by the gene and its amino acid sequence information make it possible to modify the transaldolase activity of microorganisms belonging to the genus *Corynebacterium* which are widely used in amino acid fermentation of industrial importance, to breed the microorganisms for amino acid fermentation. In addition, they also make it possible to breed strain having high transaldolase activity and are useful in stereospecific carbon—carbon bond forming reaction for production of saccharides and their derivatives.

What is claimed is:

1. An isolated DNA coding for a polypeptide comprising the amino acid sequence of SEQ ID NO:4.

2. An isolated DNA comprising the nucleotide sequence of SEQ ID NO: 2.

3. A recombinant DNA obtained by ligating the DNA of claim 1 or 2 with a vector.

4. An isolated host cell transformed with the recombinant DNA of claim 3.

5. A process for producing a polypeptide comprising the amino acid sequence of SEQ ID NO:4, said process comprising the steps of:

culturing the transformed of claim 4 in a medium to thereby produce and accumulate the polypeptide in culture, and recovering the polypeptide from the culture.

* * * * *

SEQUENCE LISTING

<160> NUMBER OF SEQ ID NOS: 6

<210> SEQ ID NO 1
<211> LENGTH: 1080
<212> TYPE: DNA
<213> ORGANISM: Corynebacterium glutamicum ATCC31388

<400> SEQUENCE: 1

```
atgtctcaca ttgatgatct tgcacagctc ggcacttcca cttggctcga cgacctctcc      60
cgcgagcgca ttacttccgg caatctcagc caggttattg aggaaaagtc tgtagtcggt     120
gtcaccacca acccagctat tttcgcagca gcaatgtcca agggcgattc ctacgacgct     180
cagatcgcag agctcaaggc cgctggcgca tctgttgacc aggctgttta cgccatgagc     240
atcgacgatg ttcgcaatgc ttgtgatctg ttcaccggca tcttcgagtc ctccaacggc     300
tacgacggcc gcgtgtccat cgaggttgac ccacgtatct ctgctgaccg cgacgcaacc     360
ctggctcagg ccaaggagct gtgggcaaag gttgatcgtc aaacgtcat gatcaagatc     420 cctgcaaccc caggttcttt gccagcaatc accgacgctt tggctgaggg catcagcgtt     480
aacgtcacct tgatcttctc cgttgctcgc taccgcgagg tcatcgctgc gtacatcgag     540
```

```
ggaatcaagc aggcagctgc aaacggccac gacgtatcca agatccactc tgtggcttcc      600
ttcttcgtct cccgcgtcga cgttgagatc gacaagcgcc tcgaggcaat cggatccgat      660
gaggctttgg ctctgcgcgg caaggcaggc gttgccaacg ctcagcgcgc ttacgctgtg      720
tacaaggagc ttttcgacgc cgccgagctg cctgaaggtg ccaacactca gcgcccactg      780
tgggcatcca ccggcgtgaa gaaccctgcg tacgctgcaa ctctttacgt ttccgagctg      840
gctggtccaa acaccgtcaa caccatgcca gaaggcacca tcgacgctgt tctggaactg      900
ggcaacctgc acggtgacac cctgtccaac tccgcggcag aagctgacgc tgtgttctcc      960
cagcttgagg ctctgggcgt tgacttggca gatgtcttcc aggtcctgga gaccgagggt     1020
gtggacaagt tgttgcttc ttggagcgaa ctgcttgagt ccatggaagc tcgcctgaag     1080
```

<210> SEQ ID NO 2
<211> LENGTH: 1080
<212> TYPE: DNA
<213> ORGANISM: Corynebacterium glutamicum ATCC31388

<400> SEQUENCE: 2

```
atgtctcaca ttgatgatct tgcacagctc ggcacttcca cttggctcga cgacctctcc       60
cgcgagcgca ttacttccgg caatctcagc caggttattg aggaaaagtc tgtagtcggt      120
gtcaccacca acccagctat tttcgcagca gcaatgtcca agggcgattc ctacgacgct      180
cagatcgcag agctcaaggc cgctggcgca tctgttgacc aggctgttta cgccatgagc      240
atcgacgatg ttcgcaatgc ttgtgatctg ttcaccggca tcttcgagtc ctccaacggc      300
tacgacggcc gcgtgtccat cgaggttgac ccacgtatct ctgctgaccg cgacgcaacc      360
ctggctcagg ccaaggagct gtgggcaaag gttgatcgtc aaacgtcat gatcaagatc       420 cctgcaaccc caggttcttt gccagcaatc accgacgctt ggctgaggg catcagcgtt      480 aacgtcacct tgatcttctc cgttgctcgc taccgcgagg tcatcgctgc gtacatcgag      540
ggaatcaagc aggcagctgc aaacggccac gacgtatcca agatccactc tgtggcttcc      600
ttcttcgtct cccgcgtcga cgttgagatc gacaagcgcc tcgaggcaat cggatccgat      660
gaggctttgg ctctgcgcgg caaggcaggc gttgccaacg ctcagcgcgc ttacgctgtg      720
tacaaggagc ttttcgacgc cgccgagctg cctgaaggtg ccaacactca gcgcccactg      780
tgggcatcca ccggcgtgaa gaaccctgcg tacgctgcaa ctctttacgt ttccgagctg      840
gctggtccaa acaccgtcaa caccatgcca gaaggcacca tcgacgctgt tctggaactg      900
ggcaacctgc acggtgacac cctgtccaac tccgcggcag aagctgacgc tgtgttctcc      960
cagcttgagg ctctgggcgt tgacttggca gatgtcttcc aggtcctgga gaccgagggt     1020
gtggacaagt tgttgcttc ttggagcgaa ctgcttgagt ccatggaagc tcgcctgaag     1080
```

<210> SEQ ID NO 3
<211> LENGTH: 4108
<212> TYPE: DNA
<213> ORGANISM: Corynebacterium glutamicum ATCC31388
<220> FEATURE:
<221> NAME/KEY: CDS
<222> LOCATION: (373)..(2472)
<220> FEATURE:
<221> NAME/KEY: CDS
<222> LOCATION: (2643)..(3722)

<400> SEQUENCE: 3

```
tcgagagttt gaaggggtcc gattcgttcc gttcgtgacg ctttgtgagg tttttgacg       60 ttgcaccgta ttgcttgccg aacatttttc ttttccttc ggttttcga gaattttcac      120
```

-continued

```
ctacaaaagc ccacgtcaca gctcccagac ttaagattgg tcacaccttt gacacatttg    180
aaccacagtt ggttataaaa tgggttcaac atcactatgg ttagaggtgt tgacgggtca    240
gattaagcaa agactacttt cggggtagat caccttttgcc aaatttgaat caattaacct   300
aagtcgtaga tctgatcatc ggatctaacg aaaacgaacc aaaactttgg tcccggttta    360
acccaggaag gaatgaccac cttgacgctg tcacctgaac ttcaggcgct cactgtacgc    420
aattacccct ctgattggtc cgatgtggac accaaggctg tagacactgt tcgtgtcctc    480
gctgcagacg ctgtagaaaa ctgtggctcc ggccacccag gcaccgcaat gagcctggct    540
ccccttgcat acaccttgta ccagcgggtt atgaacgtag atccacagga caccaactgg    600
gcaggccgtg accgcttcgt tctttcttgt ggccactcct ctttgaccca gtacatccag    660
ctttacttgg gtggattcgg ccttgagatg gatgacctga aggctctgcg cacctgggat    720
tccttgaccc caggacaccc tgagtaccgc cacaccaagg gcgttgagat caccactggc    780
cctcttggcc agggtcttgc atctgcagtt ggtatggcca tggctgctcg tcgtgagcgt    840
ggcctattcg acccaaccgc tgctgagggc gaatccccat tcgaccacca catctacgtc    900
attgcttctg atggtgacct gcaggaaggt gtcacctctg aggcatcctc catcgctggc    960
acccagcagc tggcaaccct catcgtgttc tgggatgaca accgcatctc catcgaagac   1020
aacactgaga tcgcttttcaa cgaggacgtt gttgctcgtt acaaggctta cggctggcag   1080
accattgagg ttgaggctgg cgaggacgtt gcagcaatcg aagctgcagt ggctgaggct   1140
aagaaggaca ccaagcgacc taccttcatc cgcgttcgca ccatcatcgg cttcccagct   1200
ccaaccatga tgaacaccgg tgctgtgcac ggtgctgctc ttggcgcagc tgaggttgca   1260
gcaaccaaga ctgagcttgg attcgatcct gaggctcact tcgcgatcga cgatgaggtt   1320
atcgctcaca cccgctccct cgcagagcgc gctgcacaga agaaggctgc atggcaggtc   1380
aagttcgatg agtgggcagc tgccaaccct gagaacaagg ctctgttcga tcgcctgaac   1440
tcccgtgagc ttccagcggg ctacgctgac gagctcccaa catgggatgc agatgagaag   1500
ggcgtcgcaa ctcgtaaggc ttccgaggct gcacttcagg cactgggcaa gacccttcct   1560
gagctgtggg gcggttccgc tgacctcgca ggttccaaca acaccgtgat caagggctcc   1620 ccttcctttcg gccctgagtc catctccacc gagacctggt ctgctgagcc ttacggccgt   1680
aacctgcact tcggtatccg tgagcacgct atgggatcca tcctcaacgg catttccctc   1740
cacggtggca cccgcccata cggtggaacc ttcctcatct tctccgacta catgcgtcct   1800
gcagttcgtc ttgcagctct catggagacc gacgcttact acgtctggac ccacgactcc   1860
atcggtctgg gcgaagatgg cccaacccac cagcctgttg aaaccttggc tgcgctgcgc   1920
gccatcccag gtctgtccgt cctgcgtcct gcagatgcga atgagaccgc ccaggcttgg   1980
gctgcagcac ttgagtacaa ggaaggccct aagggtcttg cactgacccg ccagaacgtt   2040
cctgttctgg aaggcaccaa ggagaaggct gctgaaggcg ttcgccgcgg tggctacgtc   2100
ctggttgagg gttccaagga aaccccagat gtgatcctca tgggctccgg ctccgaggtt   2160
cagcttgcag ttaacgctgc gaaagctctg gaagctgagg gcgttgcagc tcgcgttgtt   2220
tcagttcctt gcatggattg gttccaggag caggacgcag agtacatcga gtccgttctg   2280
cctgcagctg tgaccgctcg tgtgtctgtt gaagctggca tcgcaatgcc ttggtaccgc   2340
ttcttgggca cccagggccg tgctgtctcc cttgagcact tcggtgcttc tgcggattac   2400
cagaccctgt ttgagaagtt cggcatcacc accgatgcag tcgtggcagc ggccaaggac   2460
```

-continued

```
tccattaaca gttaattgcc ctgctgtttt tagcttcaac ccggggcagt atgattctcc    2520
ggaattttat tgccccgggt tgttgttgtt aatcggtaca aagggtctta agcacatccc    2580
ttacttgcct gctctccttg agcacagttc aagaacaatt cttttaagga aaatttagtt    2640
tcatgtctca cattgatgat cttgcacagc tcggcacttc cacttggctc gacgacctct    2700
cccgcgagcg cattacttcc ggcaatctca gccaggttat tgaggaaaag tctgtagtcg    2760
gtgtcaccac caacccagct attttcgcag cagcaatgtc caagggcgat tcctacgacg    2820
ctcagatcgc agagctcaag gccgctggcg catctgttga ccaggctgtt tacgccatga    2880
gcatcgacga tgttcgcaat gcttgtgatc tgttcaccgg catcttcgag tcctccaacg    2940
gctacgacgg ccgcgtgtcc atcgaggttg acccacgtat ctctgctgac gcgacgcaa    3000
ccctggctca ggccaaggag ctgtgggcaa aggttgatcg tccaaacgtc atgatcaaga    3060
tccctgcaac cccaggttct ttgccagcaa tcaccgacgc tttggctgag gcatcagcg    3120
ttaacgtcac cttgatcttc tccgttgctc gctaccgcga ggtcatcgct gcgtacatcg    3180
agggaatcaa gcaggcagct gcaaacggcc acgacgtatc caagatccac tctgtggctt    3240
ccttcttcgt ctcccgcgtc gacgttgaga tcgacaagcg cctcgaggca atcggatccg    3300
atgaggcttt ggctctgcgc ggcaaggcag gcgttgccaa cgctcagcgc gcttacgctg    3360
tgtacaagga gcttttcgac gccgccgagc tgcctgaagg tgccaacact cagcgcccac    3420
tgtgggcatc caccggcgtg aagaaccctg cgtacgctgc aactctttac gtttccgagc    3480
tggctggtcc aaacaccgtc aacaccatgc agaaggcac catcgacgct gttctggaac    3540
tgggcaacct gcacggtgac accctgtcca actccgcggc agaagctgac gctgtgttct    3600
cccagcttga ggctctgggc gttgacttgg cagatgtctt ccaggtcctg gagaccgagg    3660
gtgtggacaa gtttgttgct tcttggagcg aactgcttga gtccatggaa gctcgcctga    3720
agtagaatca gcacgctgca tcagtaacgg cgacatgaaa tcgaattagt tcgatcttat    3780
gtggccgtta cacatctttc attaaagaaa ggatcgtgac gctaccatcg tgagcacaaa    3840
cacgacccccc tccagctgga caaacccact gcgcgacccg caggataaac gactccccccg    3900
catcgctggc ccttccggca tggtgatctt cggtgtcact ggcgacttgg ctcgaaggaa    3960
gctgctcccc gccatttatg atctagcaaa ccgcggattg ctgccccccag gattctcgtt    4020
ggtaggttac ggccgccgcg aatggtccaa agaagacttt gaaaaatacg tacgcgatgc    4080
cgcaagtgct ggtgctcgta cggaattc                                       4108
```

<210> SEQ ID NO 4
<211> LENGTH: 360
<212> TYPE: PRT
<213> ORGANISM: Corynebacterium glutamicum ATCC31388

<400> SEQUENCE: 4

```
Met Ser His Ile Asp Asp Leu Ala Gln Leu Gly Thr Ser Thr Trp Leu
  1               5                  10                  15

Asp Asp Leu Ser Arg Glu Arg Ile Thr Ser Gly Asn Leu Ser Gln Val
             20                  25                  30

Ile Glu Glu Lys Ser Val Val Gly Val Thr Thr Asn Pro Ala Ile Phe
         35                  40                  45

Ala Ala Ala Met Ser Lys Gly Asp Ser Tyr Asp Ala Gln Ile Ala Glu
     50                  55                  60

Leu Lys Ala Ala Gly Ala Ser Val Asp Gln Ala Val Tyr Ala Met Ser
 65                  70                  75                  80
```

```
Ile Asp Asp Val Arg Asn Ala Cys Asp Leu Phe Thr Gly Ile Phe Glu
            85                  90                  95
Ser Ser Asn Gly Tyr Asp Gly Arg Val Ser Ile Glu Val Asp Pro Arg
               100                 105                 110
Ile Ser Ala Asp Arg Asp Ala Thr Leu Ala Gln Ala Lys Glu Leu Trp
            115                 120                 125
Ala Lys Val Asp Arg Pro Asn Val Met Ile Lys Ile Pro Ala Thr Pro
130                 135                 140
Gly Ser Leu Pro Ala Ile Thr Asp Ala Leu Ala Glu Gly Ile Ser Val
145                 150                 155                 160
Asn Val Thr Leu Ile Phe Ser Val Ala Arg Tyr Arg Glu Val Ile Ala
                165                 170                 175
Ala Tyr Ile Glu Gly Ile Lys Gln Ala Ala Asn Gly His Asp Val
                180                 185                 190
Ser Lys Ile His Ser Val Ala Ser Phe Phe Val Ser Arg Val Asp Val
    195                 200                 205
Glu Ile Asp Lys Arg Leu Glu Ala Ile Gly Ser Asp Glu Ala Leu Ala
    210                 215                 220
Leu Arg Gly Lys Ala Gly Val Ala Asn Ala Gln Arg Ala Tyr Ala Val
225                 230                 235                 240
Tyr Lys Glu Leu Phe Asp Ala Ala Glu Leu Pro Glu Gly Ala Asn Thr
                245                 250                 255
Gln Arg Pro Leu Trp Ala Ser Thr Gly Val Lys Asn Pro Ala Tyr Ala
                260                 265                 270
Ala Thr Leu Tyr Val Ser Glu Leu Ala Gly Pro Asn Thr Val Asn Thr
                275                 280                 285
Met Pro Glu Gly Thr Ile Asp Ala Val Leu Glu Leu Gly Asn Leu His
    290                 295                 300
Gly Asp Thr Leu Ser Asn Ser Ala Ala Glu Ala Asp Ala Val Phe Ser
305                 310                 315                 320
Gln Leu Glu Ala Leu Gly Val Asp Leu Ala Asp Val Phe Gln Val Leu
                325                 330                 335
Glu Thr Glu Gly Val Asp Lys Phe Val Ala Ser Trp Ser Glu Leu Leu
                340                 345                 350
Glu Ser Met Glu Ala Arg Leu Lys
    355                 360

<210> SEQ ID NO 5
<211> LENGTH: 700
<212> TYPE: PRT
<213> ORGANISM: Corynebacterium glutamicum ATCC31388

<400> SEQUENCE: 5

Met Thr Thr Leu Thr Leu Ser Pro Glu Leu Gln Ala Leu
            1               5                   10
Thr Val Arg Asn Tyr Pro Ser Asp Trp Ser Asp Val Asp Thr Lys Ala
    15                  20                  25
Val Asp Thr Val Arg Val Leu Ala Ala Asp Ala Val Glu Asn Cys Gly
30                  35                  40                  45
Ser Gly His Pro Gly Thr Ala Met Ser Leu Ala Pro Leu Ala Tyr Thr
                50                  55                  60
Leu Tyr Gln Arg Val Met Asn Val Asp Pro Gln Asp Thr Asn Trp Ala
            65                  70                  75
Gly Arg Asp Arg Phe Val Leu Ser Cys Gly His Ser Ser Leu Thr Gln
        80                  85                  90
```

```
Tyr Ile Gln Leu Tyr Leu Gly Gly Phe Gly Leu Glu Met Asp Asp Leu
     95                 100                 105
Lys Ala Leu Arg Thr Trp Asp Ser Leu Thr Pro Gly His Pro Glu Tyr
110                 115                 120                 125
Arg His Thr Lys Gly Val Glu Ile Thr Thr Gly Pro Leu Gly Gln Gly
                130                 135                 140
Leu Ala Ser Ala Val Gly Met Ala Met Ala Ala Arg Arg Glu Arg Gly
                145                 150                 155
Leu Phe Asp Pro Thr Ala Ala Glu Gly Glu Ser Pro Phe Asp His His
            160                 165                 170
Ile Tyr Val Ile Ala Ser Asp Gly Asp Leu Gln Glu Gly Val Thr Ser
175                 180                 185
Glu Ala Ser Ser Ile Ala Gly Thr Gln Gln Leu Gly Asn Leu Ile Val
190                 195                 200                 205
Phe Trp Asp Asp Asn Arg Ile Ser Ile Glu Asp Asn Thr Glu Ile Ala
                210                 215                 220
Phe Asn Glu Asp Val Val Ala Arg Tyr Lys Ala Tyr Gly Trp Gln Thr
            225                 230                 235
Ile Glu Val Glu Ala Gly Glu Asp Val Ala Ala Ile Glu Ala Ala Val
        240                 245                 250
Ala Glu Ala Lys Lys Asp Thr Lys Arg Pro Thr Phe Ile Arg Val Arg
    255                 260                 265
Thr Ile Ile Gly Phe Pro Ala Pro Thr Met Met Asn Thr Gly Ala Val
270                 275                 280                 285
His Gly Ala Ala Leu Gly Ala Ala Glu Val Ala Ala Thr Lys Thr Glu
                290                 295                 300
Leu Gly Phe Asp Pro Glu Ala His Phe Ala Ile Asp Asp Glu Val Ile
            305                 310                 315
Ala His Thr Arg Ser Leu Ala Glu Arg Ala Ala Gln Lys Lys Ala Ala
        320                 325                 330
Trp Gln Val Lys Phe Asp Glu Trp Ala Ala Ala Asn Pro Glu Asn Lys
    335                 340                 345
Ala Leu Phe Asp Arg Leu Asn Ser Arg Glu Leu Pro Ala Gly Tyr Ala
350                 355                 360                 365
Asp Glu Leu Pro Thr Trp Asp Ala Asp Glu Lys Gly Val Ala Thr Arg
                370                 375                 380
Lys Ala Ser Glu Ala Ala Leu Gln Ala Leu Gly Lys Thr Leu Pro Glu
            385                 390                 395
Leu Trp Gly Gly Ser Ala Asp Leu Ala Gly Ser Asn Asn Thr Val Ile
        400                 405                 410
Lys Gly Ser Pro Ser Phe Gly Pro Glu Ser Ile Ser Thr Glu Thr Trp
    415                 420                 425
Ser Ala Glu Pro Tyr Gly Arg Asn Leu His Phe Gly Ile Arg Glu His
430                 435                 440                 445
Ala Met Gly Ser Ile Leu Asn Gly Ile Ser Leu His Gly Gly Thr Arg
                450                 455                 460
Pro Tyr Gly Gly Thr Phe Leu Ile Phe Ser Asp Tyr Met Arg Pro Ala
            465                 470                 475
Val Arg Leu Ala Ala Leu Met Glu Thr Asp Ala Tyr Tyr Val Trp Thr
        480                 485                 490
His Asp Ser Ile Gly Leu Gly Glu Asp Gly Pro Thr His Gln Pro Val
    495                 500                 505
```

-continued

```
Glu Thr Leu Ala Ala Leu Arg Ala Ile Pro Gly Leu Ser Val Leu Arg
510                 515                 520                 525

Pro Ala Asp Ala Asn Glu Thr Ala Gln Ala Trp Ala Ala Leu Glu
            530                 535                 540

Tyr Lys Glu Gly Pro Lys Gly Leu Ala Leu Thr Arg Gln Asn Val Pro
                545                 550                 555

Val Leu Glu Gly Thr Lys Glu Lys Ala Ala Glu Gly Val Arg Arg Gly
            560                 565                 570

Gly Tyr Val Leu Val Glu Gly Ser Lys Glu Thr Pro Asp Val Ile Leu
            575                 580                 585

Met Gly Ser Gly Ser Glu Val Gln Leu Ala Val Asn Ala Ala Lys Ala
590                 595                 600                 605

Leu Glu Ala Glu Gly Val Ala Ala Arg Val Ser Val Pro Cys Met
            610                 615                 620

Asp Trp Phe Gln Glu Gln Asp Ala Glu Tyr Ile Glu Ser Val Leu Pro
            625                 630                 635

Ala Ala Val Thr Ala Arg Val Ser Val Glu Ala Gly Ile Ala Met Pro
            640                 645                 650

Trp Tyr Arg Phe Leu Gly Thr Gln Gly Arg Ala Val Ser Leu Glu His
            655                 660                 665

Phe Gly Ala Ser Ala Asp Tyr Gln Thr Leu Phe Glu Lys Phe Gly Ile
670                 675                 680                 685

Thr Thr Asp Ala Val Val Ala Ala Lys Asp Ser Ile Asn Ser
            690                 695                 700

<210> SEQ ID NO 6
<211> LENGTH: 360
<212> TYPE: PRT
<213> ORGANISM: Corynebacterium glutamicum ATCC31388

<400> SEQUENCE: 6

Met Ser
                                                          1

His Ile Asp Asp Leu Ala Gln Leu Gly Thr Ser Thr Trp Leu Asp Asp
        5                  10                  15

Leu Ser Arg Glu Arg Ile Thr Ser Gly Asn Leu Ser Gln Val Ile Glu
        20                  25                  30

Glu Lys Ser Val Val Gly Val Thr Thr Asn Pro Ala Ile Phe Ala Ala
35                  40                  45                  50

Ala Met Ser Lys Gly Asp Ser Tyr Asp Ala Gln Ile Ala Glu Leu Lys
                55                  60                  65

Ala Ala Gly Ala Ser Val Asp Gln Ala Val Tyr Ala Met Ser Ile Asp
            70                  75                  80

Asp Val Arg Asn Ala Cys Asp Leu Phe Thr Gly Ile Phe Glu Ser Ser
            85                  90                  95

Asn Gly Tyr Asp Gly Arg Val Ser Ile Glu Val Asp Pro Arg Ile Ser
            100                 105                 110

Ala Asp Arg Asp Ala Thr Leu Ala Gln Ala Lys Glu Leu Trp Ala Lys
115                 120                 125                 130

Val Asp Arg Pro Asn Val Met Ile Lys Ile Pro Ala Thr Pro Gly Ser
                135                 140                 145

Leu Pro Ala Ile Thr Asp Ala Leu Ala Glu Gly Ile Ser Val Asn Val
            150                 155                 160

Thr Leu Ile Phe Ser Val Ala Arg Tyr Arg Glu Val Ile Ala Ala Tyr
            165                 170                 175
```

-continued

```
Ile Glu Gly Ile Lys Gln Ala Ala Asn Gly His Asp Val Ser Lys
        180             185             190
Ile His Ser Val Ala Ser Phe Phe Val Ser Arg Val Asp Val Glu Ile
195                 200             205             210
Asp Lys Arg Leu Glu Ala Ile Gly Ser Asp Glu Ala Leu Ala Leu Arg
                215             220             225
Gly Lys Ala Gly Val Ala Asn Ala Gln Arg Ala Tyr Ala Val Tyr Lys
            230             235             240
Glu Leu Phe Asp Ala Ala Glu Leu Pro Glu Gly Ala Asn Thr Gln Arg
        245             250             255
Pro Leu Trp Ala Ser Thr Gly Val Lys Asn Pro Ala Tyr Ala Ala Thr
        260             265             270
Leu Tyr Val Ser Glu Leu Ala Gly Pro Asn Thr Val Asn Thr Met Pro
275             280             285             290
Glu Gly Thr Ile Asp Ala Val Leu Glu Leu Gly Asn Leu His Gly Asp
                295             300             305
Thr Leu Ser Asn Ser Ala Ala Glu Ala Asp Ala Val Phe Ser Gln Leu
            310             315             320
Glu Ala Leu Gly Val Asp Leu Ala Asp Val Phe Gln Val Leu Glu Thr
        325             330             335
Glu Gly Val Asp Lys Phe Val Ala Ser Trp Ser Glu Leu Leu Glu Ser
        340             345             350
Met Glu Ala Arg Leu Lys
355             360
```